United States Patent

Toriida et al.

[11] Patent Number: 5,922,888
[45] Date of Patent: *Jul. 13, 1999

[54] PROCESS FOR REMOVAL OF DIOL AS IMPURITY IN CYCLIC CARBONIC ACID ESTER

[75] Inventors: Masahiro Toriida; Akio Hiwara; Keiichi Yokoyama, all of Sodegaura, Japan

[73] Assignee: Mitsui Petrochemical Industries, Ltd., Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/624,985

[22] Filed: Mar. 29, 1996

[30] Foreign Application Priority Data

Mar. 31, 1995 [JP] Japan .................................. 7-076259

[51] Int. Cl.$^6$ ...................... C07D 317/36; C07D 319/06
[52] U.S. Cl. ............................................ 549/228; 549/230
[58] Field of Search ............................. 549/228, 230

[56] References Cited

U.S. PATENT DOCUMENTS 3,846,450  11/1974  Stalker et al. ........................ 549/230
5,091,543   2/1992  Grey ..................................... 549/228
5,436,362   7/1995  Kondoh et al. ....................... 558/277

FOREIGN PATENT DOCUMENTS

0614240A1  9/1994  European Pat. Off. .
5-74485    3/1993  Japan .
7048320    2/1995  Japan .

OTHER PUBLICATIONS

XP 000576836, pp. 19–24, 1982.

*Primary Examiner*—Laura L. Stockton
*Attorney, Agent, or Firm*—Birch, Stewart, Kolasch & Birch, LLP

[57] ABSTRACT

A process for removing a diol from a cyclic carbonic acid ester containing the diol as an impurity, which comprises bringing a cyclic carbonic acid ester containing a diol as an impurity into contact with a synthetic zeolite in the presence of a chain carbonic acid ester. According to this process, there can be obtained a mixture of a cyclic carbonic acid ester and a chain carbonic acid ester having a very small content of diol, which is suitable as a solvent for electrolytic solution of a condenser, cell or battery.

8 Claims, No Drawings

PROCESS FOR REMOVAL OF DIOL AS IMPURITY IN CYCLIC CARBONIC ACID ESTER

BACKGROUND OF THE INVENTION

1. Field of the Invention

The present invention relates to a process for removing a diol present as an impurity in a cyclic carbonic acid ester (cyclic carbonate). The present invention further relates to a mixture of a cyclic carbonic acid ester and a chain carbonic acid ester (non-cyclic carbonate), which is obtained by the above process and contains less diols as the impurities.

2. Prior Art

Cyclic or chain carbonic acid esters have been and are used, for example, as a solvent for polymers, or a solvent for various chemical reactions, or a solvent for electrolytic solution of a condenser, cell or battery. These carbonic acid esters contain, as impurities, monohydric alcohols such as methanol, ethanol and the like, and dihydric alcohols (diols) such as ethylene glycol, diethylene glycol, propylene glycol and the like. In particular, cyclic carbonic acid esters inevitably contain, as impurities, ethylene glycol and diethylene glycol (in the case of synthesizing ethylene carbonate) and propylene glycol (in the case of synthesizing propylene carbonate), since they are generally synthesized from oxides or diols,. When a carbonic acid ester is used, for example, as a solvent for electrolytic solution of cell or battery, the diols present as impurities in the carbonic acid ester adversely affect the storage properties, etc. of the cell or battery.

Japanese Patent Application Kokai (Laid-Open) No. 74,485/1993 discloses a cyclic carbonic acid ester-containing solvent as a solvent for non-aqueous electrolytic solution, and a method for reducing the diol content in said solvent to 1,500 ppm by weight or less by subjecting said cyclic carbonic acid ester to an adsorption treatment with a molecular sieve. In the method, however, the removal of diol is not sufficient because diols generally have molecular sizes larger than the pore diameters of the adsorption sites of molecular sieve.

SUMMARY OF THE INVENTION

An object of the present invention is to provide a process for removing a diol from a cyclic carbonic acid ester containing the diol as an impurity, simply and efficiently.

Other object of the present invention is to provide a mixture of a cyclic carbonic acid ester and a chain carbonic acid ester, which scarcely contains a diol as an impurity; and a process for obtaining said mixture.

The present invention firstly provides a process for removing a diol from a cyclic carbonic acid ester containing the diol as an impurity, which comprises contacting a cyclic carbonic acid ester containing a diol as an impurity, with a synthetic zeolite in the presence of a chain carbonic acid ester.

The present invention secondly provides a mixture of a cyclic carbonic acid ester and a chain carbonic acid ester, which is obtained by the above process and hardly has a diol content as an impurity.

The present invention thirdly provides a process for producing a mixed solvent of a cyclic carbonic acid ester and a chain carbonic acid ester, which comprises (1) mixing a cyclic carbonic acid ester containing a diol as an impurity and a chain carbonic acid ester and (2) bringing the resulting mixture into contact with a synthetic zeolite to remove a diol to a great extent.

The objects and advantages of the present invention are achieved by the above inventions. The present invention is described in detail below, whereby the other objects and advantages of the present invention will be made apparent.

DETAILED DESCRIPTION OF THE INVENTION

There is no particular restriction as to the cyclic carbonic acid ester containing, as an impurity, a diol to be removed by the present process. A typical example of the cyclic carbonic acid ester is a five-membered cyclic carbonic acid ester represented by the following general formula (1):

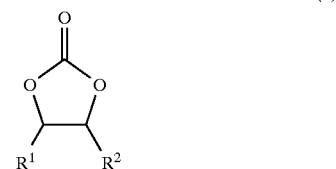

(1)

and a six-membered cyclic carbonic acid ester represented by the following general formula (2):

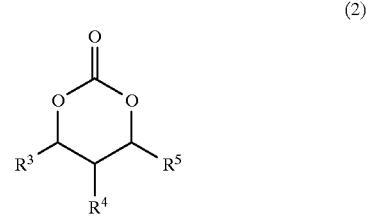

(2)

In the above general formulas (1) and (2), $R^1$, $R^2$, $R^3$, $R^4$ and $R^5$ are each independently a straight- or branched-chain alkyl group having 1 to 4 carbon atoms, such as a methyl, ethyl, propyl, isopropyl, isobutyl, sec-butyl or tert-butyl group; a cycloalkyl group having 3 to 4 carbon atoms, such as a cyclopropyl or cyclobutyl group; or a hydrogen atom.

As the carbonic acid ester to be purified, the cyclic carbonic acid ester (C) represented by the Reaction formula (I) described later is also included.

Specific examples of the cyclic carbonic acid ester include ethylene carbonate, 1,2-propylene carbonate, 2,3-butylene carbonate, 1,3-propylene carbonate, 1,2-butylene carbonate, 2,4-pentylene carbonate, 1,3-pentylene carbonate and the like. Among these, ethylene carbonate, 1,2-propylene carbonate, 1,3-propylene carbonate are preferred. The cyclic carbonic acid ester may be a single carbonic acid ester or a mixture of two or more carbonic acid esters.

The diol contained as an impurity in the cyclic carbonic acid ester may be a remaining diol used as a starting material in cyclic carbonic acid ester production or formed from an oxide also used as a starting material in the cyclic carbonic acid ester production, the remaining diol being not removed through the purification and remaining in the cyclic carbonic acid ester. When the cyclic carbonic acid ester is, for example, ethylene carbonate, the diol as an impurity may be ethylene glycol and diethylene glycol; when the cyclic carbonic acid ester is propylene carbonate, the diol may be propylene glycol; and when the cyclic carbonic acid ester is butylene carbonate, the diol may be butylene glycol. The content of the diol in the cyclic carbonic acid ester varies depending upon the kind of the cyclic carbonic acid ester, while it is generally 100 to 20,000 ppm by weight.

According to the process of the present invention, the cyclic carbonic acid ester containing a diol as an impurity is brought into contact with a synthetic zeolite in the presence of a chain carbonic acid ester to remove the diol.

The present inventors have found out that in the above contact treatment, a diol (A) and a chain carbonic acid ester (B) are subjected to ester interchange represented by the following reaction formula (I), by the catalysis of the synthetic zeolite, whereby a cyclic carbonic acid ester (C) and mono-alcohols ($D^1$) and ($D^2$) are formed.

[Reaction formula (I)]

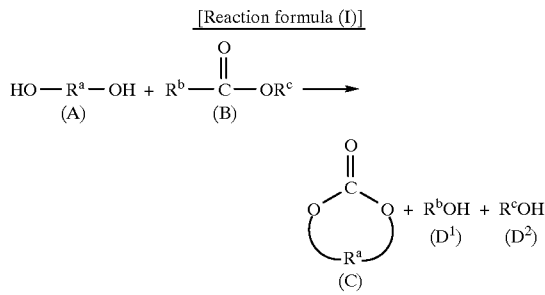

The present inventors further found out that the formed monoalcohols are adsorbed by the synthetic zeolite. Although the above ester exchange reaction itself is a reversible reaction, the equilibrium shifts to the right side because the synthetic zeolite adsorbs the monoalcohols. As a result, the reaction proceeds to the arrow direction.

In the reaction formula (I), $R^a$ may be a bivalent residue of diol, for example, a bivalent residue represented by the following formula (3), (4) or (5):

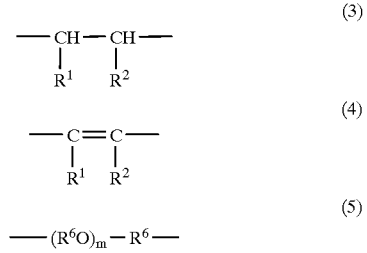

wherein $R^1$ and $R^2$ have the same definitions as in the formula (1); and when m is 0, $R^6$ is a straight- or branched-chain alkylene group having 3 to 15, preferably 1 to 6, carbon atoms, and when m is an integer of 1 to 3, is a straight- or branched-chain alkylene group having 1 to 15, preferably 1 to 6, carbon atoms. $R^b$ and $R^c$ may be each independently a monovalent hydrocarbon group, for example, a straight- or branched-chain alkyl group having 1 to 3 carbon atoms, or a cycloalkyl group having 3 to 4 carbon atoms.

The synthetic zeolite not only acts as a catalyst for the reaction represented by the reaction formula (I) but also adsorbs the monoalcohols formed as side products in the reaction and serves to promote the reaction.

The contact of the cyclic carbonic acid ester containing a diol as an impurity, with a synthetic zeolite in the presence of a chain carbonic acid ester brings about (a) the reaction represented by the reaction formula (I) and further (b) the adsorption of the monoalcohols formed as side products in the reaction, by the synthetic zeolite, and consequently, the diol is removed.

The chain carbonic acid ester used in the process of the present process is not particularly restricted as long as the above reaction proceeds. A typical example of the chain carbonic acid ester is represented by the following general formula (6):

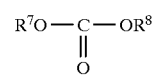

wherein $R^7$ and $R^8$ are each independently a straight- or branched-chain alkyl group having 1 to 4 carbon atoms, such as a methyl, ethyl, propyl, isopropyl, isobutyl, sec-butyl or tert-butyl group, or a cycloalkyl group having 3 or 4 carbon atoms, such as a cyclopropyl group or cyclobutyl group. At least one hydrogen atom of the above alkyl group may be substituted by halogen atom(s) (F, Cl, etc.).

Specific examples of the chain carbonic acid ester include dimethyl carbonate, diethyl carbonate, methyl ethyl carbonate, dipropyl carbonate, methyl propyl carbonate, ethyl propyl carbonate, dibutyl carbonate, methyl butyl carbonate, ethyl butyl carbonate, propyl butyl carbonate, diisopropyl carbonate, methyl isopropyl carbonate, ethyl isopropyl carbonate, diisobutyl carbonate, methyl isobutyl carbonate, ethyl isobutyl carbonate, propyl isobutyl carbonate, isopropyl isobutyl carbonate, dicyclopropyl carbonate, methyl cyclopropyl carbonate, ethyl cyclopropyl carbonate, dicyclobutyl carbonate, methyl cyclobutyl carbonate, ethyl cyclobutyl carbonate, propyl cyclobutyl carbonate and methyl (2,2,2-trifluoroethyl) carbonate. These esters can be used singly or in combination of two or more.

Among them, dimethyl carbonate, methyl ethyl carbonate and/or diethyl carbonate are/is particularly preferably used.

In the process of the present invention, the amount of the chain carbonic acid ester used is not be particularly restricted. However, it is preferable that in the contact with a synthetic zeolite, the chain carbonic acid ester is present in a proportion of 1/99 or more, preferably 10/90 to 90/10, more preferably 20/80 to 80/20 in terms of (chain carbonic acid ester/cyclic carbonic acid ester) weight ratio.

The synthetic zeolite is known per se as a so-called molecular sieve and is commercially available. There are many kinds of synthetic zeolites which are different in chemical composition and pore diameter of adsorption site; and they are classified into molecular sieves of 3A type, 4A type, 5A type, 13X type, etc. depending upon the pore diameter of adsorption site. In the process of the present invention, any of 3A type, 4A type, 5A type and 13X type can be selected depending upon the kinds of the monoalcohols $R^7OH$ and $R^8OH$ formed in the reaction formula (I).

When the chain carbonic acid ester is dimethyl carbonate, diethyl carbonate or methyl ethyl carbonate, the monoalcohol(s) formed in the above reaction is (are) methanol or/and ethanol and, therefore, there can be preferably used a synthetic zeolite of 5A type capable of adsorbing molecules having effective diameters of 5 Å or less, or a synthetic zeolite of 13X type capable of adsorbing molecules having effective diameters of 10 Å or less.

Synthetic zeolites have water of crystallization in some cases. In such cases, they are preferably dried beforehand to remove the water. There is no particular restriction as to the drying method, and any drying method ordinarily used can be used. It includes, for example, drying using direct fire, steam or an electric furnace.

In the present process, there is no particular restriction as to the method for conducting contact with synthetic zeolite, but preferable methods include the followings:

(1) a method which comprises continuously passing a uniform mixture solution of a cyclic carbonic acid ester and a chain carbonic acid ester, which has been beforehand prepared by mixing a cyclic carbonic acid ester and a chain carbonic acid ester, through a column or cylindrical reactor filled with a synthetic zeolite and (2) a method which comprises adding a synthetic zeolite to a uniform mixture solution of a cyclic carbonic acid ester and a chain carbonic acid ester, which has been beforehand prepared by mixing a cyclic carbonic acid ester and a chain carbonic acid ester, in a batchwise manner and then allowing the resulting mixture to stand or stirring the mixture.

The contact temperature is preferably appropriately room temperature (about 20° C.) to 80° C.

The contact time differs depending upon the kind and concentration of diol, the kind of chain carbonic acid ester, the extent of diol removal, the contact temperature, the kind and amount of zeolite, etc. However, when the above method (1) is used with a view of increasing the diol removal rate, the contact is conducted so that the liquid hourly space velocity (LHSV) preferably becomes about 1 to 30 $hr^{-1}$. When the method (2) is used, the contact time is generally 30 minutes to 24 hours and the amount of the zeolite used is preferably 1 to 20% by weight based on the total of the cyclic carbonic acid ester and the chain carbonic acid ester.

Needless to say, the operation of the above method (1) or (2) may be conducted a plurality of times in the case where the amount of the diol contained in the cyclic carbonic acid ester is large, for example, 2,500 ppm by weight or more based on the cyclic carbonic acid ester.

In the contact with the synthetic zeolite, small amounts of compounds such as ether, ester, carbamate and the like may be present as long as the amounts do not hinder the proceeding of the above reaction and the adsorption of monoalcohol by zeolite. The amounts of such compounds are preferably 10 parts by weight or less per 100 parts by weight based on the total of the cyclic carbonic acid ester and the chain carbonic acid ester.

By the above contact, the content of the diol as an impurity can be reduced to 60 ppm by weight or less relative to the total amount of the cyclic carbonic acid ester and the chain carbonic acid ester.

After the contact with the synthetic zeolite, there is obtained a mixture of a cyclic carbonic acid ester and a chain carbonic acid ester, which has a very small content of a diol.

A cyclic carbonic acid ester containing a small amount of a diol can be obtained by subjecting the mixture to an isolation step, for example, a distillation step. In order to obtain a cyclic carbonic acid ester having a smaller content of the diol, it is preferable to use a mixture containing a chain carbonic acid ester having a boiling point sufficiently different from that of the cyclic carbonic acid ester.

The mixture of a cyclic carbonic acid ester and a chain carbonic acid ester, which has been obtained by the contact with a synthetic zeolite and contains a diol in a very small amount, for example, 60 ppm by weight or less, preferably 10 ppm by weight or less relative to the total amount of the two carbonic acid esters, can be used per se as a solvent for electrolytic solution of condenser, cell, battery or the like. In this case, the preferable combinations of the cyclic carbonic acid ester and the chain carbonic acid ester are as follows, for example.

(1) A combination wherein the cyclic carbonic acid ester is 1,2-propylene carbonate and the chain carbonic acid ester is dimethyl carbonate, methyl ethyl carbonate, diethyl carbonate, methyl n-propyl carbonate or methyl isopropyl carbonate.

(2) A combination wherein the cyclic carbonic acid ester is ethylene carbonate and the chain carbonic acid ester is the same as in the above combination (1).

(3) A combination wherein the cyclic carbonic acid ester is 1,2-propylene carbonate and the chain carbonic acid ester is dimethyl carbonate and methyl ethyl carbonate; dimethyl carbonate and diethyl carbonate; dimethyl carbonate and methyl n-propyl carbonate; dimethyl carbonate and methyl isopropyl carbonate; methyl ethyl carbonate and diethyl carbonate; methyl ethyl carbonate and methyl n-propyl carbonate; methyl ethyl carbonate and methyl isopropyl carbonate; diethyl carbonate and methyl n-propyl carbonate; diethyl carbonate and methyl isopropyl carbonate; or methyl n-propyl carbonate and methyl isopropyl carbonate.

(4) A combination wherein the cyclic carbonic acid ester is ethylene carbonate and the chain carbonic acid ester is the same as in the above combination (3).

(5) A combination wherein the cyclic carbonic acid ester is a mixture of 1,2-propylene carbonate and ethylene carbonate, and the chain carbonic acid ester is dimethyl carbonate, methyl ethyl carbonate, diethyl carbonate, methyl n-propyl carbonate or methyl isopropyl carbonate.

The present invention is hereinafter described specifically by way of Examples. However, the present invention is in no way restricted to these Examples.

In the following Examples and Comparative Examples, the measurement of impurity content was conducted using a gas chromatograph (Model 5890, a product of Yokogawa-Hewlett-Packard, Ltd.). The column used was DB-624 Capillary Column (a product of J & W Co.).

The diol contents in each of the cyclic carbonic acid esters used in Examples and Comparative Examples are shown in Table 1.

EXAMPLE 1

3,000 ml of a carbonic acid ester mixture containing 38 parts by weight of ethylene carbonate as the cyclic carbonic acid ester, 62 parts by weight of dimethyl carbonate as the chain carbonic acid ester and, as impurities, 1,220 ppm by weight of ethylene glycol and 520 ppm by weight of diethylene glycol was passed through a column filled with 30 g of Molecular Sieve 5A (a product of Union Showa K. K.) at room temperature (20° C.) to bring the carbonic acid ester mixture into contact with the molecular sieve (a synthetic zeolite). In this case, the inside diameter of the column was 20 mm; the length of the molecular sieve layer was 20 cm; and the liquid hourly space velocity (LHSV) was 6 $hr^{-1}$.

In the carbonic acid ester mixture after the contact treatment, the ethylene glycol content was 12 ppm by weight and the diethylene glycol content was 24 ppm by weight, and the amounts of these diols as impurities were drastically reduced compared with those before the contact.

The methanol as a by-product formed by the reaction of dimethyl carbonate with ethylene glycol and the reaction of dimethyl carbonate with diethylene glycol was not detected. This indicates that the methanol formed as a by-product was adsorbed by the molecular sieve (a synthetic zeolite).

EXAMPLE 2

A carbonic acid ester mixture containing 75 parts by weight of ethylene carbonate, 25 parts by weight of dimethyl carbonate and, as impurities, 1,450 ppm by weight of ethylene glycol and 750 ppm by weight of diethylene glycol was subjected to the same treatment as in Example 1. The amounts of impurities in the carbonic acid ester mixture after treatment are shown in Table 2.

EXAMPLE 3

A carbonic acid ester mixture having a composition shown in Table 2 was subjected to the same treatment as in Example 1. The amounts of impurities in the carbonic acid ester mixture after treatment are shown in Table 2.

EXAMPLE 4

A carbonic acid ester mixture containing 53 parts by weight of 1,2-propylene carbonate as the cyclic carbonic acid ester, 47 parts by weight of dimethyl carbonate as the chain carbonic acid ester and 1,320 ppm by weight of 1,2-propylene glycol as an impurity was subjected to the same treatment as in Example 1. The amounts of impurities in the carbonic acid ester mixture after treatment are shown in Table 2.

Comparative Example 1

1,2-Propylene carbonate, as the cyclic carbonic acid ester, containing 1,830 ppm by weight of 1,2-propylene glycol as an impurity was subjected to the same treatment as in Example 1. The 1,2-propylene carbonate after treatment contained 1,824 ppm by weight of 1,2-propylene glycol and hence, there was no decrease of impurity content.

In the following Tables, the abbreviations refer to the followings.

PC: propylene carbonate
EC: ethylene carbonate
DEC: diethyl carbonate
DEG: diethylene glycol
DMC: dimethyl carbonate
EG: ethylene glycol
PG: propylene glycol
N.D.: not detected

TABLE 1

| | Cyclic carbonic acid ester | Diol content (ppm) | | |
| --- | --- | --- | --- | --- |
| | | EG | DEG | PG |
| Example 1 | EC | 1220 | 520 | — |
| Example 2 | EC | 1450 | 750 | — |
| Example 3 | EC | 1380 | 660 | — |
| Example 4 | PC | — | — | 1320 |
| Comparative Example 1 | PC | — | — | 1830 |

EXAMPLE 5

Into a Schlenk type reactor were charged 13.5 g (0.15 mole) of dimethyl carbonate (DMC), 3.10 g (0.05 mole) of ethylene glycol (EG) and 1.72 g of Molecular Sieve 5A (dried at 350° C., a product of Union Showa K. K.). The contents in the reactor were heated at 60° C. for 6 hours in a nitrogen atmosphere. After the completion of the heating, a sample was taken from the reaction mixture and subjected to a gas chromatography analysis. The results are shown in Table 3.

TABLE 3

| Components of reaction mixture | Area in gas chromatogram chart (%) |
| --- | --- |
| DMC | 81.51 |
| EG | 12.62 |
| EC | 1.89 |

As is clear from the above results, ethylene carbonate (EC), which is a cyclic carbonate, is formed by reacting dimethyl carbonate with ethylene glycol in the presence of a synthetic zeolite.

As is clear from the above tests, according to the present process wherein a cyclic carbonic acid ester containing a diol is brought into contact with a synthetic zeolite in the presence of a chain carbonic acid ester, the chain carbonic acid ester and the diol cause an ester exchange reaction by the catalytic action of the synthetic zeolite to form a cyclic carbonic acid ester and a monoalcohol and the mono-alcohol formed is adsorbed by the synthetic zeolite; as a result, the amount of the diol contained as an impurity in the cyclic carbonic acid ester can be significantly reduced. Thus, there can be obtained a mixture of a cyclic carbonic acid ester and a chain carbonic acid ester, which has a very small content of a diol. This mixture is suitable as various organic solvents, especially as a solvent for electrolytic solution of a condenser, cell or battery.

TABLE 2

Composition of carbonic acid ester mixture

| | Cyclic carbonic acid ester | | Chain carbonic acid ester | | | Impurities (ppm) | | | |
| --- | --- | --- | --- | --- | --- | --- | --- | --- | --- |
| | Kind | Parts by weight | Kind | Parts by weight | | EG | DEG | PG | MeOH |
| Example 1 | EC | 38 | DMC | 62 | Before treatment | 1,220 | 520 | — | — |
| | | | | | After treatment | 12 | 24 | — | N.D. |
| Example 2 | EC | 75 | DMC | 25 | Before treatment | 1,450 | 750 | — | — |
| | | | | | After treatment | 10 | 28 | — | N.D. |
| Example 3 | EC | 58 | DMC | 42 | Before treatment | 1,380 | 660 | — | — |
| | | | | | After treatment | 18 | 34 | — | N.D. |
| Example 4 | PC | 53 | DMC | 47 | Before treatment | — | — | 1,320 | — |
| | | | | | After treatment | — | — | 45 | N.D. |
| Comparative Example 1 | PC | 100 | — | — | Before treatment | — | — | 1,830 | — |
| | | | | | After treatment | — | — | 1,824 | N.D. |

What is claimed is:

1. A process for removing a diol from a cyclic carbonic acid ester solution containing the diol as an impurity, which comprises the following steps:
   (1) mixing the cyclic carbonic acid ester solution containing a diol as an impurity, and a chain carbonic acid ester; and then
   (2) bringing the resulting mixture into contact with a synthetic zeolite, wherein the diol is converted to mono-alcohol, which is adsorbed to the zeolite.

2. A process according to claim 1, wherein the cyclic carbonic acid ester is at least one member selected from the group consisting of ethylene carbonate, 1,2-propylene carbonate, 1,2-butylene carbonate, 1,3-propylene carbonate and 2,3-butylene carbonate.

3. A process according to claim 1, wherein the chain carbonic acid ester is at least one member selected from the group consisting of dimethyl carbonate, methyl ethyl carbonate and diethyl carbonate.

4. A process according to claim 1, wherein the cyclic carbonic acid ester is ethylene carbonate or 1,2-propylene carbonate and the chain carbonic acid ester is dimethyl carbonate.

5. A process according to claim 1, wherein in the contact treatment the chain carbonic acid ester is present in a proportion of 90/10 to 10/90 in terms of (chain carbonic acid ester/cyclic carbonic acid ester) weight ratio.

6. A process according to claim 1, wherein the contact reduces the diol content to 60 ppm by weight or less based on the total amount of the cyclic carbonic acid ester and the chain carbonic acid ester.

7. A process according to claim 1, wherein the synthetic zeolite is a molecular sieve of 3A, 4A, 5A or 13X type.

8. The process according to claim 1, wherein the cyclic carbonic acid ester solution containing a diol as an impurity contains the diol in an amount of 100 to 20,000 ppm by weight.

* * * * *